United States Patent [19]

Arnhem

[11] 4,308,947
[45] Jan. 5, 1982

[54] CONTACT LENS HOLDING AND APPLICATOR DEVICE

[76] Inventor: Erik M. Arnhem, 4113 Beverly Blvd., Los Angeles, Calif. 90004

[21] Appl. No.: 120,538

[22] Filed: Feb. 11, 1980

Related U.S. Application Data

[63] Continuation-in-part of Ser. No. 82,811, Oct. 9, 1979.

[51] Int. Cl.³ .................. B65D 85/00; B08B 3/10; A61F 9/00; A45C 11/04
[52] U.S. Cl. .................. 206/5.1; 294/1 CA
[58] Field of Search ............ 206/5.1, 537; 294/1 CA; 132/80 R

[56] References Cited

U.S. PATENT DOCUMENTS 2,818,872  1/1958  Wensan ........................ 132/80 R
3,063,083  1/1962  Obitts ............................. 206/5.1
4,244,466  1/1981  Arnhem ......................... 206/5.1

Primary Examiner—William T. Dixson, Jr.
Attorney, Agent, or Firm—Erik M. Arnhem

[57]  ABSTRACT

Contact lens applicator, comprising a container with closure, an apertured contact lens accommodating tray extending from the closure for placement within the container, a contact lens retaining member slidable over the tray and provided with apertures which may be brought in alignment with those of the tray.

2 Claims, 4 Drawing Figures

U.S. Patent  Jan. 5, 1982  4,308,947
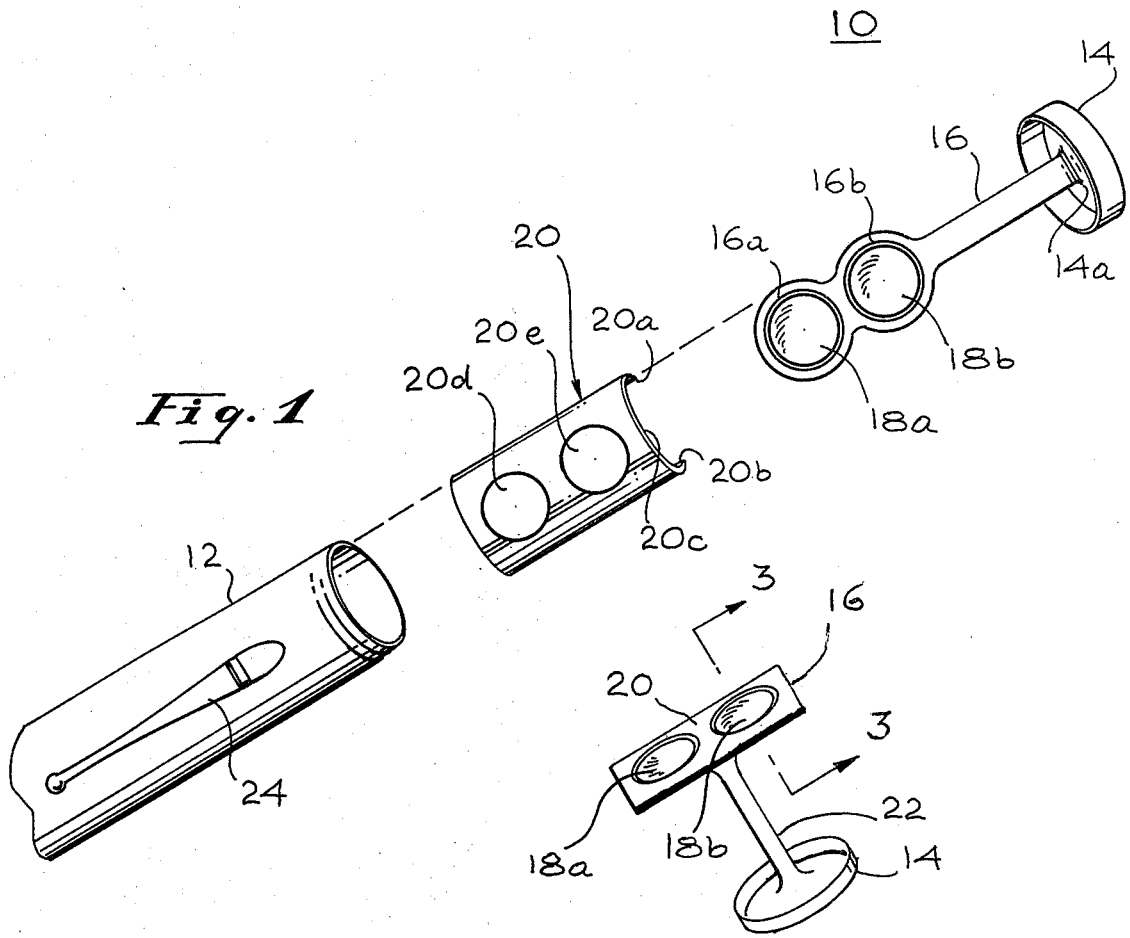
Fig. 1
Fig. 2
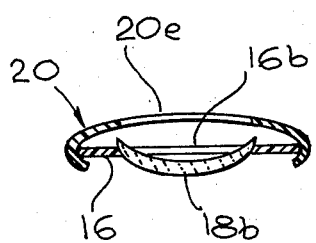
Fig. 3
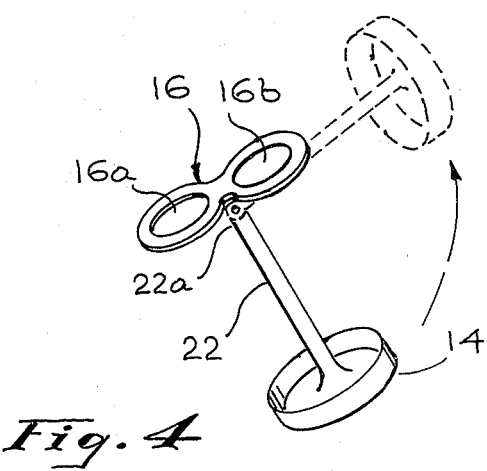
Fig. 4

CONTACT LENS HOLDING AND APPLICATOR DEVICE

CROSS REFERENCES TO RELATED APPLICATIONS

This application is a continuation-in-part application of parent application Ser. No. 082,811, filed Oct. 9, 1979 in the Patent Office.

FIELD OF THE INVENTION

Several drawbacks exist with respect to cleaning and applying a contact lens onto the eyeball, especially when the contact lens wearer has no immediate access to tap water.

Firstly, it is extremely important that the hands be washed thoroughly prior to touching the contact lens so as not to cause an infection to the eye.

Secondly, when applying the contact lens, the latter is placed on a fingertip and the clarity of the outer lens surface will be adversely affected by the moisture or secretions of the finger.

Thirdly, when a contact lens has been applied and float on the cornea of the eye, the wearer of the lens frequently experiences a pain or discomfort in the eye, normally caused by a tiny foreign object, e.g., a hair trapped between the inner surface of the lens and the cornea, or by a film of mucus forming on the lens; if this occurs when the contact lens wearer is driving a car, or works at a location where water is not readily available, the contact lens wearer must remove, and somehow try to clean and reinsert the lens with contaminated hands.

There is, therefore a need to conceive a device which will enable the contact lens wearer—when e.g., getting up in the morning, during work, driving, etc.—to clean and reinsert a contact lens without direct manipulation.

The container for the applicator, according to the invention, is furthermore less bulky than the conventional leak proof contact lens container and, additionally incorporates means for storing and actually cleaning the contact lens within the container and applying same directly onto the eye from the applicator; moreover, the danger of losing a contact lens while cleaning or handling same is virtually eliminated by avoiding direct manipulation of a wetted lens.

It should also be noted, that the conventional contact lens storage/cleansing container is not used for actively cleaning the lens but merely causes the latter to float in a chemical solution poured into the container.

SUMMARY OF THE INVENTION

In addition to what is stated, the device, according to the invention, entails a new concept in the storage/cleansing of and applying a contact lens. Contrary to the present way of placing contact lenses in a storage/cleaning container, the invention provides for a narrow apertured tray, mounted to and extending vertically (or horizontally by the intermediary of a vertical rodlet) from the cap or closure of and into a container; the contact lens may then be positioned vertically suspended in an appropriately dimensioned aperture in the tray, with the interior lens surface facing outwardly and lying substantially flush with or slightly above the periphery of the aperture.

An apertured sliding member is provided, intended for sliding over the tray, causing, when required for the objectives of the invention, the aperture(s) of the slide to coincide with that/those of the tray, and thus lock the lens in an aperture of the tray, or, alternately, to be removed from and thus fully expose the lens accommodated in the aperture of the tray.

By virtue of the coinciding apertures of the tray and sliding member, water or storage/cleaning fluid may reach all surfaces of the contact lens accommodated in the tray. The diameters of the apertures of the tray and sliding member are substantially identical or may be decreasing somewhat in depth relative to or perhaps slightly smaller than the diameter of the contact lens, and the latter thus cannot escape through either of the overlapping apertures, but is locked there within.

Furthermore, an elongated center portion of the sliding member may be raised or curved slightly, that is preferably at a height substantially identical to or slightly smaller than that of the contact lens, forming an open ended channel along the length of the sliding member, so that the fluid, additionally may flow through the thusly created channel onto the interior surface of the contact lens. Since the height of the raised center portion of the sliding member is equal to or less than that of the contact lens, the latter may, when subjected to fluid pressure from below, rise slightly in its apertured seat in the tray, but cannot—regardless of the width of the channel of the sliding member—slip through same. Furthermore, the plastic lens (when wetted) will, at any rate cling to the applicator, which, preferably is made of an appropriate plastic material, and this is so, even when the sliding member has been removed from the tray, on which the lens is accommodated.

Thus, when the contact lens is in place in the aperture of the tray and the sliding member is properly superposed on the tray, cleaning or storage fluid in the container is capable of effectively reaching all areas of the contact lens, being subjected to a swishing action of the fluid.

Due to the suspended vertical position of the contact lens (or lenses) in the container, the dimensions of the latter may be extremely narrow, as small as, e.g., 8 mm (depth)×15 mm (width)×40 mm (length). The container for the contact lens(es) may, then, if provided with a holder or clip, be carried as a pen in a shirt pocket, bag, etc., without risking leakage or fluid therefrom.

Such a container may actually incorporate a real writing instrument, which, when in use, could carry out a swishing cleansing action of the fluid therein.

Thus, the device, according to the invention, carries out effective cleansing of a contact len as well as serving as an applicator of the lens directly to the eye without manually touching same. The described features of the device are, as noted, of particular importance, when the contact lens wearer does not have access to water for cleaning of hands and lenses.

It is, therefore an object of the invention to provide a self-contained device for storing and cleaning of and direct transferring contact lenses therefrom to the eyes, respectively.

It is a further object of the invention to provide such a device, so dimensioned that it may be carried in the pocket as a pen or the like.

It is still a further object to provide such a device which will require a minimum of manual handling of the contact lenses accommodated therein.

BRIEF DESCRIPTION OF THE DRAWINGS

FIG. 1 is an exploded perspective view of the device, according to the invention, comprising a container, with a closure from which a tray extends, and a sliding member, slidable over the tray.

FIG. 2 is a perspective view of the tray and sliding member superposed thereon in an embodiment differing somewhat from that of FIG. 1.

FIG. 3 is a sectional view of tray and sliding member on line 3—3 of FIG. 2, with a contact lens seated in the tray.

FIG. 4 is a perspective view of the device, (without sliding member) according to the invention, in an embodiment substantially as the one shown in FIG. 2.

EMBODIMENTS OF THE INVENTION

In the drawings like reference numbers indicate identical parts in the various views thereof. In the drawings, numeral 10 indicates the device or housing, according to one embodiment of the applicator, in its entirety. As illustrated in the drawings; housing means, e.g., a container 12 for the contact lenses (FIG. 1) is of cylindric shape and closure 14 may be adapted to be screwed onto the container, or otherwise appropriately fastened thereto. Container 12 and closure 14 may, of course be of any suitable shape, such as oval, rectangular, etc., that is adaptable to the purpose underlying the invention.

Means for accommodating and ocularly inserting the contact lens(es) e.g., a narrow thin tray 16 is, in FIG. 1, mounted perpendicularly to (or extends integrally from) preferably, an off-centered interior portion of closure 14 and becomes inserted in container 12 when closure 14 is mounted over the opening of the container. The primary reason for the trays 16 off-centered position relative to closure 14 is to facilitate the direct transfer of the contact lens(es) therefrom to the eye(s). Tray 16 is apertured, e.g., provided with two apertures 16a, 16b, spaced appropriately from one another. The diameter of apertures 16a or 16b is approximately 10 mm (or 5/16 of an inch), in the case that a standard sized 10 mm (5/16") diameter lens 18 is intended for accommodation therein. The preferred length and width of tray 16 are, respectively 40–60 mm, 15 mm and 8 mm. The interior surface of contact lens 18 is, when placed in aperture 16a or b of tray 16, facing upwardly (FIG. 3). Due to the relative dimensions of contact lens 18 and aperture 16a or b, the upper rim of the former will lie substantially flush with, or slightly above the periphery of aperture 16a or b, and cannot drop through aperture 16a, b.

The surface of tray 16, lying closest to the outer edge or rim of closure 14 is considered, for the purpose of explaining the drawings, the top surface from which contact lens 18 is transferred to the eye, and subsequently returned to for cleansing and storage.

Removable retaining means for the contact lens(es), e.g., a sliding member 20, is provided with downward and inwardly directed surfaces forming a longitudinal open-ended passage, e.g., channels 20a, 20b, into which the edges of tray 16 slides, so that tray 16 will underlie the top surface of sliding member 20; furthermore, sliding member 20 may have a slightly raised or curved open-ended center portion 20c, extending along the entire length of the upper surface of sliding member 20, the preferred length of which is about 30-40 mm.

Sliding member 20 is apertured, e.g., provided with two apertures 20d, e, spaced apart from one another at the same distance as between aperture 16a, b of tray 16, which are intended to coincide with the apertures of the latter. The diameter of apertures 20d, e, is substantially identical to or slightly smaller than that of contact lens 18, so that the latter—when positioned in apertures 16a, b, and apertures 20d, e and 16a, b, respectively are caused to coincide with each other—cannot either escape through apertures 20d, e. The height of the raised portion 20c of sliding member 20 is less or substantially identical to that of contact lens 18 and therefore the latter can also not pass through the raised portion 20c (FIG. 1).

Thus, all surfaces of contact lens 18 are accessible to the cleansing fluid, to be poured into container 12, even the rim portion of contact lens 18, due to the clearance provided by the raised center portion 20c of sliding member 20. When sliding member 20 is removed from or pushed backwardly relative to tray 16, the contact lens(es) will be fully exposed in apertures 16a, b, ready for direct application therefrom to the eye(s).

In FIG. 1, the container for the applicator, according to the invention, is shaped as a pen with holding means, e.g., a clip 22, for convenient attachment to a pocket, or the like.

FIG. 2 illustrates another embodiment of the invention. In contrast to the arrangement described in FIG. 1, tray 16 does not extend vertically from closure 14, but parallel thereto via the intermediary of a rodlet 22, mounted to closure 14 so that tray 16 and slide 20 if placed horizontally within a container will require a container of wider dimensions that the one shown in FIG. 1; tray 16 (as shown in FIG. 2) is manipulated by closure 14 or holding handle 22, extending perpendicularly from the underside of tray 16, preferably from between apertures 16a, b. Rodlet 22 may be provided with pivotal means, as clearly seen in FIG. 4, for the accommodation within narrow container 12 (FIG. 1).

In FIG. 4, rodlet 22, adjacent its end mounted to tray 16, shows the pivoting means, e.g, a hinged connection 22a, so that rodlet 22 terminating in closure 14 may be swung (indicated by arrow) towards and in substantial alignment with the underside of tray 16 for vertical placement therewith, and within container 12. When rodlet 22 is in its aligned position it will only touch an outer edge portion of slide 20, or tray 16, and thus, will not impact with a contact lens therein. A vertical positioning of tray 16 within container, will permit the use of a very narrow container.

The suggested mode of operating the applicator is as follows:

(1) The lens(es) should be wiped or rinsed clean prior to being placed on the apertured tray 16 of the device.

(2) Slide 20 is then slit over the tray 16, so that is aperture(s) overlap(s) the aperture(s) of tray 16, interlocking the lens(es) on the tray.

(3) Tray 16 and superposed slide 20 are then placed in container 12 of cleaning/storage fluid, with closure 14 (extending from tray 12 or rodlet 22) tightly sealing off the container.

(4) The fluid, will when swished vigorously in container 12, cleanse or maintain the lenses in a wetted and clean condition for subsequent applications to the eyes.

(5) To apply the lenses, one removes the lens interlocking tray from the container, and then the slide 20 from the aperture(s) of tray 16; in the case of a lens for the right eye, one holds closure 14 with the right hand, and brings the lens 18 in aperture 16a very close to the right eye, causing the pupil of the eye to follow the light behind aperture 16a, while at the same time, e.g., the thumb and index finger of the left hand separates the upper and lower eye lids; the lens will then transfer to and be properly placed on the eye ball.

The same steps are repeated when applying a lens to the left eye, except, of course, the left hand will be holding tray 16, etc.

Obviously, one may use any other convenient method of applying the lenses, as directed by an optometrist or physician.

As it appears from the above description, the device according to the invention, may not only be used as a contact lens cleaning and applying device in "emergency" situations, (e.g., no access to tap water) but also under normal conditions, in which case the contact lens wearer, e.g., at bedtime may, subsequent to removing clean the lens(es) thoroughly and then place them in the applicator, for immediate application, e.g., in the morning, without first again subjecting the lenses to manual rubbing, rinsing, etc.

It would also—prior to insertion of a lens—be possible to rinse, rub and clean the contact lenses under tap tap water while retained between tray 16 and slide 20, thus, minimizing the manipulation or possibility of losing a lens.

While the foregoing has illustrated and described what is now contemplated to be the best mode of carrying out the invention, the description is, of course, subject to modifications without departing from the spirit and scope of the invention. Therefore, it is not desired to restrict the invention to the particular construction illustrated and described, but to cover all modifications that may fall within the scope of the appended claims.

I claim:
1. In a device for contact lenses, comprising:
   (a) means for ocularly applying contact lenses accommodated thereon;
   (b) contact lens retaining means mountable on the contact lens applying means;
   (c) holding means for the contact lens applying and retaining means;
   (d) closing means mountable on the housing means;
   (e) a rodlet, one end of which is mounted to and extends perpendicularly from the closing means, the other end of the rodlet being mounted to the contact lens applying means for manipulation thereof.
2. Device for contact lenses, according to claim 1, wherein the rodlet adjacent its point of mounting with the contact lens applying means, is provided with pivoting means, so that the rodlet may be swung towards the contact lens applying means for substantial alignment therewith and accommodation within the housing means.

* * * * *